(12) United States Patent
Girod et al.

(10) Patent No.: US 10,098,676 B2
(45) Date of Patent: Oct. 16, 2018

(54) SURGICAL IMPLANT FOR FUSION BETWEEN TWO BONE PORTIONS AND A CLAMPING ANCILLARY FOR CLAMPING SUCH A SURGICAL IMPLANT

(71) Applicant: NOVASTEP, St Gregoire (FR)

(72) Inventors: Loïc Girod, Goven (FR); Grégory Gledel, Paris (FR); Gilles Audic, Pleumeleuc (FR); Marc Augoyard, Tassin la Demi Lune (FR); Romain Augoyard, Tassin la Demi Lune (FR); Tristan Meusnier, Saint Etienne (FR); Stéphanie Valentin, Lyons (FR)

(73) Assignee: NOVASTEP, St Gregoire (FR)

( * ) Notice: Subject to any disclaimer, the term of this patent is extended or adjusted under 35 U.S.C. 154(b) by 262 days.

(21) Appl. No.: 15/125,474

(22) PCT Filed: Mar. 10, 2015

(86) PCT No.: PCT/FR2015/050591
§ 371 (c)(1),
(2) Date: Sep. 12, 2016

(87) PCT Pub. No.: WO2015/136212
PCT Pub. Date: Sep. 17, 2015

(65) Prior Publication Data
US 2017/0065310 A1 Mar. 9, 2017

(30) Foreign Application Priority Data
Mar. 11, 2014 (FR) ..................................... 14 51980

(51) Int. Cl.
*A61B 17/72* (2006.01)
*A61B 17/68* (2006.01)
(Continued)

(52) U.S. Cl.
CPC .......... *A61B 17/7291* (2013.01); *A61B 17/68* (2013.01); *A61B 17/7266* (2013.01);
(Continued)

(58) Field of Classification Search
CPC ..................... A61B 17/7291; A61B 17/7266
See application file for complete search history.

(56) References Cited

U.S. PATENT DOCUMENTS

| 5,358,405 A | * | 10/1994 | Imai | A61C 5/00 433/215 |
| 8,262,712 B2 | * | 9/2012 | Coilard-Lavirotte | A61B 17/1604 606/300 |

(Continued)

FOREIGN PATENT DOCUMENTS

| FR | 2846545 A1 | 5/2004 |
| FR | 2856269 A1 | 12/2004 |
| FR | 2901119 A1 | 11/2007 |

OTHER PUBLICATIONS

Jul. 7, 2015 International Search Report issued in International Patent Application No. PCT/FR2015/050591.

*Primary Examiner* — Andrew Yang
(74) *Attorney, Agent, or Firm* — Oliff PLC

(57) ABSTRACT

A surgical implant which includes: a first anchoring portion comprising two first arms movable between an inserting position and an anchoring position, in which the first arms are spread apart so as to be anchored in a first bone; a second anchoring portion to be anchored in the second bone; and an intermediate portion connecting the first anchoring portion to the second anchoring portion. The intermediate portion comprises: a recess; and a first connecting portion and a second connecting portion that are remote from one another. Bringing the first connecting portion and second connecting (Continued)

portion closer together moves the first arms from the inserting position thereof to the anchoring position thereof.

14 Claims, 4 Drawing Sheets

(51) Int. Cl.
  *A61B 17/88* (2006.01)
  *A61F 2/42* (2006.01)
(52) U.S. Cl.
  CPC ...... *A61B 17/8863* (2013.01); *A61B 17/8872* (2013.01); *A61F 2002/4228* (2013.01); *A61F 2002/4243* (2013.01)

(56) References Cited

U.S. PATENT DOCUMENTS

| | | | |
|---|---|---|---|
| 8,394,097 B2* | 3/2013 | Peyrot | A61F 2/30 606/62 |
| 8,475,456 B2* | 7/2013 | Augoyard | A61B 17/68 606/331 |
| 9,522,022 B2* | 12/2016 | Cheney | A61B 17/7266 |
| 9,545,274 B2* | 1/2017 | McCormick | A61B 17/7291 |
| 2003/0233095 A1* | 12/2003 | Urbanski | A61F 2/0805 606/916 |
| 2011/0301653 A1 | 12/2011 | Reed et al. | |
| 2012/0083791 A1 | 4/2012 | Cheney et al. | |

\* cited by examiner

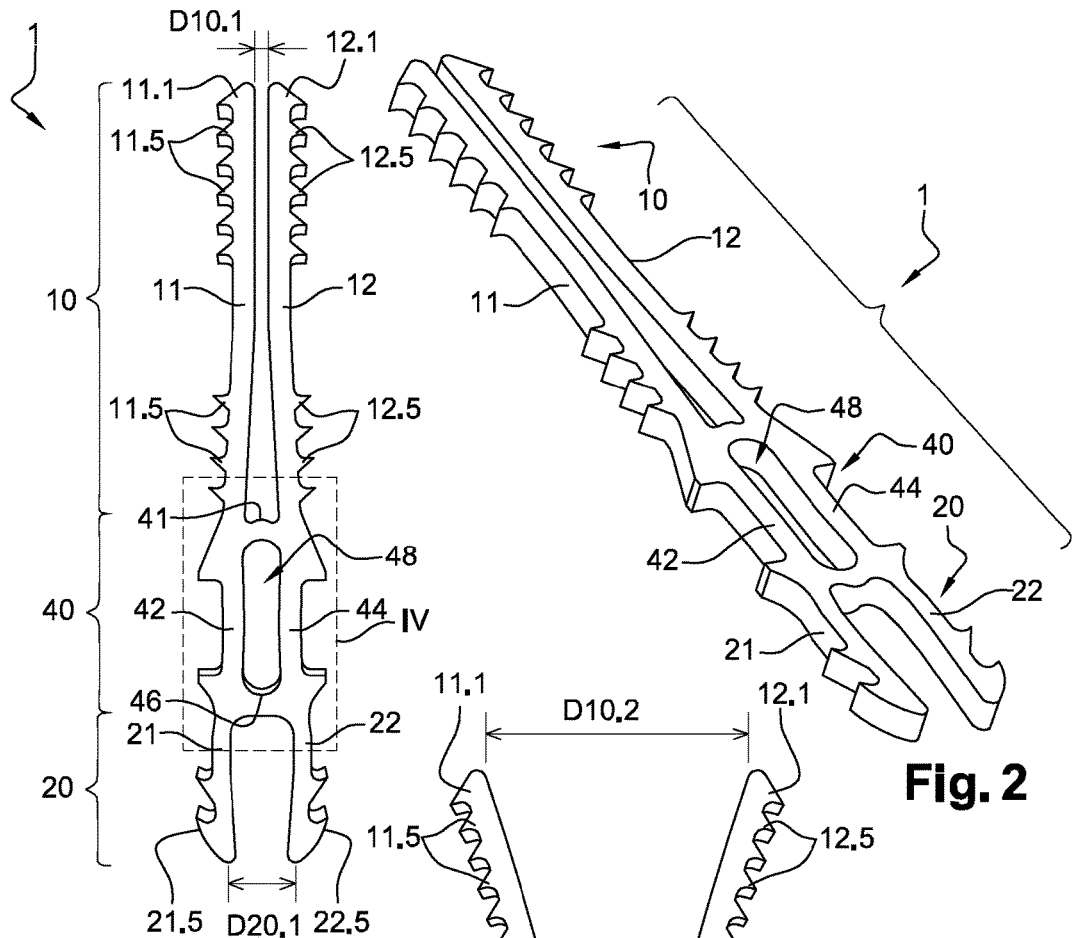
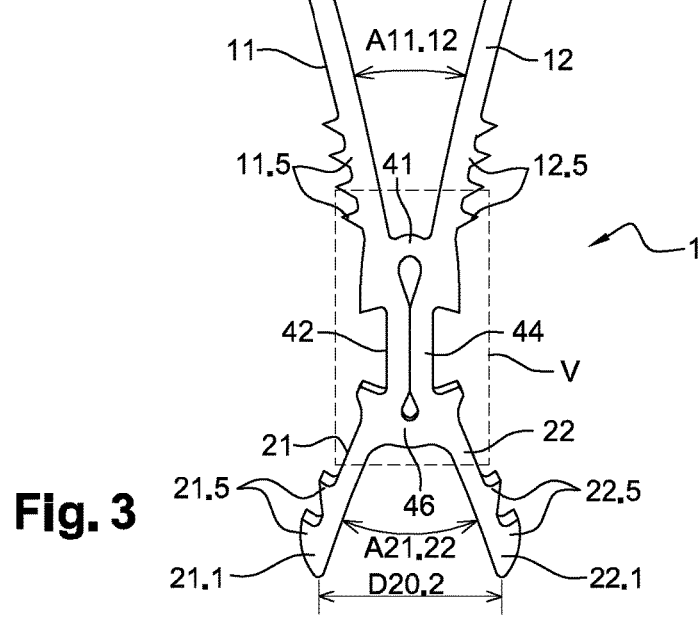
Fig. 1
Fig. 2
Fig. 3

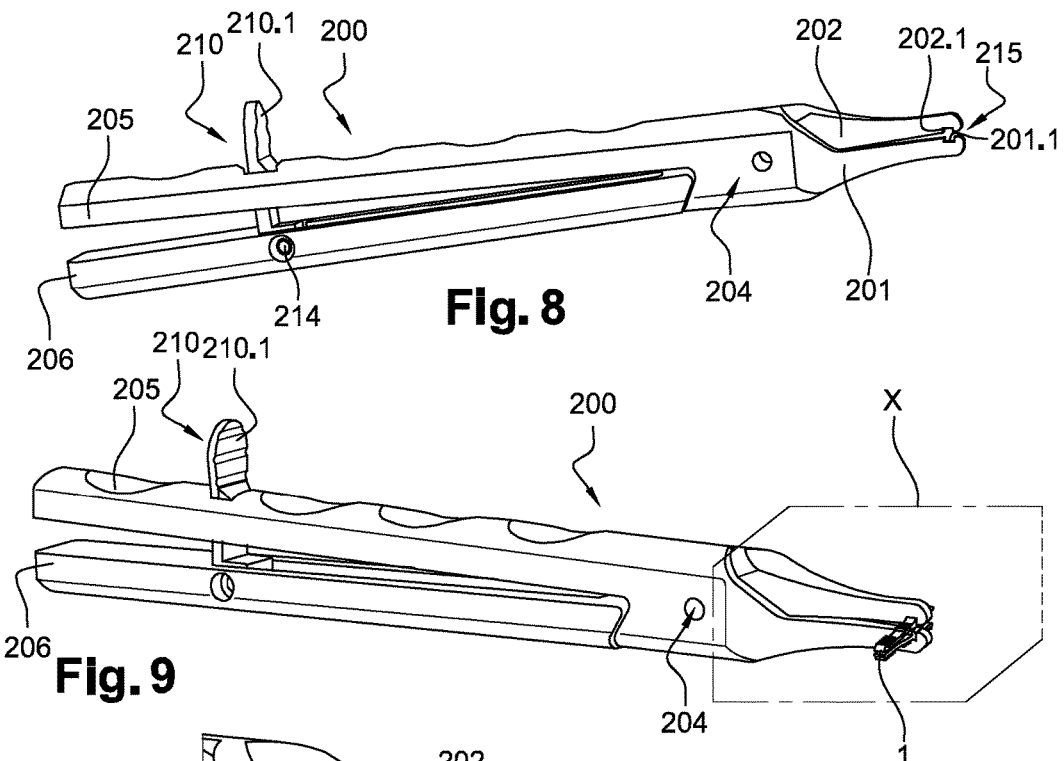
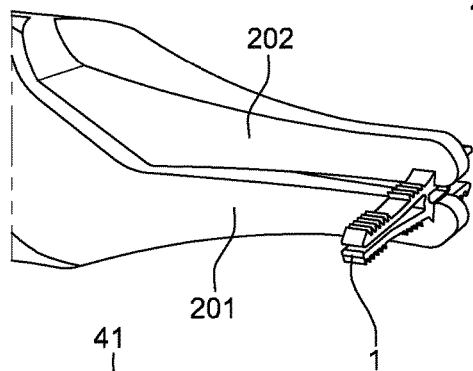
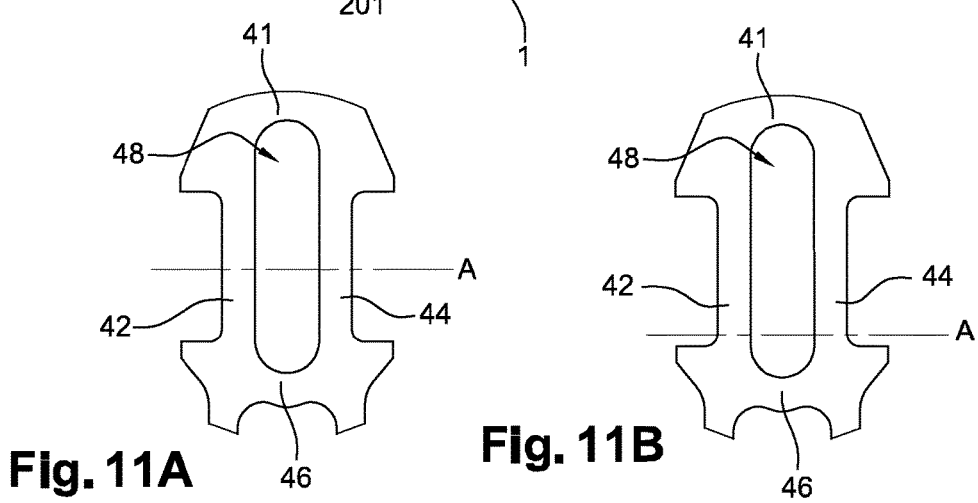

SURGICAL IMPLANT FOR FUSION BETWEEN TWO BONE PORTIONS AND A CLAMPING ANCILLARY FOR CLAMPING SUCH A SURGICAL IMPLANT

The present invention concerns a surgical implant intended to enable fusion between a first bone portion and a second bone portion. In addition, the present invention concerns a clamping ancillary, configured to clamp a surgical implant. In a known manner, an ancillary is a handling instrument intended to assist the medical personnel.

The present invention may be applied to the field of surgical implants used to carry out an arthodesis by intramedullary bone fusion in a joint. The present invention may also be applied to the field of surgical implants used for an osteosynthesis through fusion between two bone fragments. The indications are for example:

The correction of claw toes by arthrodesis of the proximal and/or distal interphalangeal joint of the foot, the surgical treatment of osteoarthritis or traumas by arthrodesis of the proximal and distal interphalangeal joints of the foot, the surgical treatment of osteoarthritis or traumas by arthrodesis of the proximal and distal interphalangeal joints of the hand, anosteosynthesis by fusion of two bone fragments, in particular of the foot or of the hand.

The document FR2846545A1 illustrates a surgical implant which is made of a shape-memory alloy. This surgical implant comprises two anchoring portions, configured to be anchored respectively in a first bone and in a second bone, and an intermediate portion connecting the anchoring portions together. The branches of each anchoring portion are displaceable between:

an introduction position, in which the branches are close to each other and can be introduced in a respective bone, the surgical implant thereby having generally a «H» shape, and an anchoring position, in which the branches are spaced apart further than in the introduction position, so that the branches anchor each anchoring portion in a respective bone, the surgical implant thereby having generally an «X» shape.

However, since the surgical implant of FR2846545A1 is composed of a shape-memory alloy, it is necessary to refrigerate it for several hours in order to place it in the introduction position before its implantation. Then, the surgeon has only a short time period to implant this surgical implant before its branches return back in the anchoring position under the shape-memory effect. Hence, this short time period might alter the accuracy of the positioning of the surgical implant in the bones. In addition, the shorter is this time period, the more the surgical implant recovers little by little its final shape, thereby making difficult or still impossible the insertion of the surgical implant at the bone site.

The present invention aims in particular to solve all or part of the aforementioned problems. For this purpose, an object of the invention is a surgical implant, intended to enable fusion between a first bone portion and a second bone portion, the surgical implant comprising at least:

a first anchoring portion configured to be anchored in the first bone portion, the first anchoring portion including at least two first branches, the first branches being displaceable between:

an introduction position, in which the respective ends of the first branches define a first introduction distance, so as to enable the introduction of the first branches inside the first bone portion, and an anchoring position, in which the respective ends of the first branches define a first anchoring distance larger than the first introduction distance, so that the first branches are adapted to anchor the first anchoring portion inside the first bone portion, a second anchoring portion configured to be anchored in the second bone portion, an intermediate portion connecting the first anchoring portion to the second anchoring portion;

the surgical implant being characterized in that:

the intermediate portion includes at least:

a recess, a first linking portion disposed between the first anchoring portion and the second anchoring portion, and a second linking portion disposed between the first anchoring portion and the second anchoring portion, the first linking portion and the second linking portion being arranged on either side of said at least one recess so that the first linking portion is distant from the second linking portion, and the intermediate portion is shaped so that, bringing together the first linking portion and the second linking portion, displaces the first branches from their introduction position to their anchoring position.

In other words, bringing together the first linking portion and the second linking portion reduces said at least one recess, thereby displacing the first branches.

Advantageously, said at least one recess presents a closed contour. Alternatively, said at least one recess may present a partially-closed contour; for example, said at least one recess may be open along 10 or 20% of its periphery.

According to one variant of the invention, the first linking portion extends substantially between the first branch and the second anchoring portion, and the second linking portion extends substantially between the second branch and the second anchoring portion.

According to one variant of the invention, the first introduction distance may be zero or negligible.

According to one embodiment of the invention, the second anchoring portion includes at least two second branches, the second branches being displaceable between:

an introduction position, in which the respective ends of the second branches define a second introduction distance, so as to enable the introduction of the second branches inside the second bone portion, and an anchoring position, in which the respective ends of the second branches define a second anchoring distance larger than the second introduction distance, so that the second branches are adapted to anchor the second anchoring portion inside the second bone portion, and wherein the intermediate portion is shaped so that bringing together the first linking portion and the second linking portion displaces the second branches from their introduction position to their anchoring position.

In other words, the surgical implant has at least four branches, namely at least two at each side of the intermediate portion. Thus, such a surgical implant allows for a firm and simple anchorage not only in the first bone portion, but also in the second bone portion.

According to one variant of the invention, the second introduction distance may be zero or negligible.

Alternatively, the second anchoring portion includes one single branch configured to be anchored in the second bone portion. This single branch may be formed for example by an anchoring rod.

According to one variant of the invention, the first branches are longer than the second branches. For example, the ratio between a length of the first branches and a length of the second branches is comprised between 1.5 and 5. The length of each first branch may be comprised between 5 mm and 20 mm. The length of each second branch may be comprised between 3 mm and 10 mm. The intermediate portion may have a length, measured along the longitudinal direction of a first branch, comprised between 3 mm and 10 mm.

According to one variant of the invention, the intermediate portion, the first anchoring portion and the second anchoring portion have thicknesses comprised between 0.5 mm and 2 mm. According to one variant of the invention, the first anchoring portion includes at least three first branches, for example four first branches. In this case, the intermediate portion includes several respective joining portions arranged so as to join the first branches at least in pairs. Thus, such a first anchoring portion allows carrying out a three-dimensional anchorage, which may have a very high mechanical strength and an excellent stability.

According to one embodiment of the invention, the intermediate portion is plastically deformable so that a plastic deformation of the intermediate portion bringing together the first linking portion and the second linking portion displaces the first branches and/or the second branches from their introduction position(s) to their anchoring position(s).

In other words, a mechanical stress applied to the intermediate portion is determined so as to produce a permanent or irreversible deformation of the intermediate portion.

Thus, this plastic deformation, which is by definition irreversible and permanent, allows a surgeon to easily place the first branches and/or the second branches in the anchoring position(s). In addition, the surgeon has all the time necessary to accurately position the surgical implant in the first bone portion and in the second bone portion, which guarantees to the patient a resistant and durable anchorage of the surgical implant. Advantageously, the plastic deformation is carried out in the field of homogeneous plastic deformation of the material composing the intermediate portion. Thus, such a homogeneous plastic deformation avoids weakening by stricture the intermediate portion, thereby preserving a high mechanical strength.

According to one variant of the invention, the intermediate portion is plastically deformable so that a plastic deformation of the intermediate portion bringing into contact the first linking portion and the second linking portion displaces the first branches from the introduction position to the anchoring position. In other words, after the plastic deformation, the first linking portion touches the second linking portion. Thus, when clamping with a specific clamping ancillary, the surgeon can feel at which moment he should stop clamping the intermediate portion.

According to one embodiment of the invention, alternatively to a plastic deformation, the intermediate portion is elastically deformable so that an elastic expansion of the intermediate portion bringing together the first linking portion and the second linking portion displaces the first branches from their introduction position(s) to their anchoring position(s).

In other words, a mechanical stress applied to the intermediate portion is determined so as to produce a reversible deformation of the intermediate portion. The intermediate portion is pre-stressed prior to the introduction of the surgical implant in the body of the patient, then this pre-stress is released completely or partially so as to reach the anchoring position in the body of the patient.

Thus, the intermediate portion is elastically deformable between i) a high elastic deformation position, in which the first branches and/or the second branches are in the introduction position(s), and ii) a low or zero elastic deformation position, in which the first branches and/or the second branches are in the anchoring position(s).

According to one variant of the invention, the surgical implant is configured to cooperate with retaining means movable between:
 a retaining position, in which the retaining means retain the elastically deformed intermediate portion, and
 a release position, in which the retaining means release the intermediate portion so that said elastic expansion can intervene.

For example, the retaining means may comprise a stud, which, when in the retaining position, is inserted in said at least one recess. When the stud is removed, the elastic expansion of the intermediate portion brings the first linking portion closer to the second linking portion, thereby displacing the first branches and/or the second branches toward their anchoring position(s).

According to one embodiment of the invention, each of the first branches has a generally elongated shape, and the first branches are substantially parallel in their introduction position and form substantially a «V» in their anchoring position. In other words, the first branches form a tightened «U» in the introduction position and a «V» in the anchoring position. The «V» shape is defined by an angular sector which is advantageously comprised between 20 degrees and 60 degrees.

According to one variant of the invention, each of the second branches has a generally elongated shape, the second branches are substantially parallel in their introduction position, and the second branches form substantially a «V» in their anchoring position. In other words, in this variant, the surgical implant has generally a tightened «H» shape in the introduction positions and an «X» shape in the anchoring positions.

Thus, such shapes allow for an easy introduction and a firm anchorage of the surgical implant in the first bone portion and in the second bone portion. According to one variant of the invention, the first branches extend along a first longitudinal direction, the second branches extend along a second longitudinal direction, the first branches and the second branches forming an angle comprised between 150 degrees and 180 degrees in a plane containing the first longitudinal direction and the second longitudinal direction. According to one embodiment of the invention, the intermediate portion further includes i) a first joining portion joining at least two first branches, and ii) a second joining portion joining at least two second branches, the first linking portion and the second linking portion being arranged respectively on either side of the first joining portion and on either side of the second joining portion. In this embodiment, the first linking portion, the second linking portion, the first joining portion and the second joining portion define said at least one recess. Thus, the intermediate portion may present a high mechanical strength and allow for a high geometrical accuracy of the deformation.

According to one variant of the invention, the first linking portion and the second linking portion define at least one recess presenting a closed contour defined by the first linking portion, by the second linking portion, by the first joining portion and by the second joining portion. Thus, such a closed recess allows for a high geometrical accuracy of the deformation.

Alternatively, the intermediate portion presents a recess having a contour open toward the second anchoring portion.

According to one variant of the invention, said at least one recess contains an element more deformable than the intermediate portion. To this end, the elastic or plastic deformation limit of the material composing this element is lower than the plastic deformation limit of the material composing the intermediate portion. Thus, the element does not prevent nor does it slow down the plastic deformation bringing the first linking portion closer to the second linking portion. This element may be composed for example of a polymer material.

According to one embodiment of the invention, at least one recess has an oblong shape, the length of which extends generally between the first anchoring portion and the second anchoring portion.

Thus, such an oblong recess requires a short plastic deformation stroke, and therefore a limited clamping from the surgeon.

According to one embodiment of the invention, at least one recess presents a narrow area and a large area which is larger than the narrow area, the widths being measured between the first linking portion and the second linking portion.

In particular, the widths are measured transversely to a longitudinal direction along which the first branches extend.

For example, this recess may present approximately, in a top view, a pear or bicycle saddle shape. Thus, such a dissymmetrical shape allows a displacement of the first branches larger than the displacement of the second branches, so as to adapt the surgical implant to specific indications.

According to one embodiment of the invention, the first linking portion presents a first face which is convex and which is oriented toward the second linking portion, the first face having a profile formed by an arc of circle the radius of which is larger than 20 mm, preferably larger than 40 mm, and the second linking portion presents a second face which is convex and which is oriented toward the first linking portion, the second face having a profile formed by an arc of circle the radius of which is larger than 20 mm, preferably larger than 40 mm.

Thus, such arcs of circle allow obtaining, during a plastic deformation, a high geometrical accuracy in the displacement of the first branches and, if appropriate, of the second branches.

Advantageously, the radius of the circular profiles are equal.

According to one variant of the invention, the first introduction distance is comprised between 0 and 2 mm, and the first anchoring distance is comprised between 1 and 10 mm.

Thus, such dimensions are particularly adapted to the interphalangeal joints of feet or hands.

According to one variant of the invention, the second introduction distance is comprised between 0 and 2 mm, and the second anchoring distance is comprised between 1 and 10 mm.

According to one embodiment of the invention, at least the intermediate portion is composed of a material selected in the group constituted by:
  a titanium alloy, preferably a grade 1, 2, 3 or 4 alloy, according to the standard ISO 5832-2 or ASTM F67, and
  a stainless steel according to the standard ISO 5832-1.

For example, the intermediate portion made of such a titanium alloy presents a plastic deformation range with a high tensile strength and a relatively low yield strength, which allows obtaining the plastic deformation with a slight compressive force.

According to one variant of the invention, at least one among the first branches and the second branches presents, on a respective outer face, notches configured for the anchorage of the surgical implant respectively in the first bone portion and in the second bone portion.

Advantageously, on the or each end portion of a respective first or second branch, there are notches in the form of harpoons.

According to one embodiment of the invention, the intermediate portion further includes at least two abutments extending in protrusion on two opposite outer faces of the intermediate portion.

Thus, the abutments allow positioning accurately a clamping ancillary on the intermediate portion.

According to one variant of the invention, in the case where the second anchoring portion comprises second branches, the intermediate portion includes four abutments, namely two abutments located on the side of the first branches and two abutments located on the side of the second branches. Advantageously, the abutments located on the side of the first branches are larger than the abutments located on the side of the second branches.

Advantageously, outer faces of the intermediate portion present, next to the abutments, friction means configured to grip, by friction, the jaws of a clamping ancillary. For example, these friction means may comprise notches or roughnesses.

Moreover, an object of the present invention is a clamping ancillary, configured to clamp at least one surgical implant according to the invention, the clamping ancillary comprising at least two jaws and at least one joint connecting said at least two jaws, the clamping ancillary being characterized in that each jaw presents a respective housing having a shape complementary to a respective linking portion so as to grip a respective outer face of the intermediate portion, and in that said at least one joint is configured so that a displacement of the jaws results in bringing together the first linking portion and the second linking portion.

Thus, such a clamping ancillary allows clamping the surgical implant until obtaining the aforementioned plastic deformation.

According to one embodiment of the invention, said at least one joint includes a latch presenting at least one locking notch, the joint being movable between:
  an open position, in which the jaws define a space allowing the installation of the surgical implant,
  a retaining position, in which the jaws grip the respective outer faces of the intermediate portion so that the clamping ancillary retains the surgical implant,
  a clamping position, in which the jaws clamp the intermediate portion so as to obtain said approximation.

According to one embodiment of the invention, the latch is linked to one of the jaws by a pivot link, and the latch presents a handling portion, configured to allow a surgeon to handle the latch so as to move the joint between the open position, the retaining position and the clamping position.

The embodiments and the variants mentioned hereinbefore may be considered separately or according to any technically permissible combination.

The present invention will be better understood and its advantages will appear in the light of the description that follows, given only as a non-limiting example and made with reference to the appended drawings, in which:

FIG. 1 is a front view of a surgical implant in accordance with the invention, in the introduction configuration;

FIG. 2 is a perspective view of the surgical implant of FIG. 1, in the introduction configuration;

FIG. 3 is a front view of the surgical implant of FIG. 1, in the anchoring configuration;

FIG. 8 is a perspective view of a clamping ancillary in accordance with the invention and configured to hold then clamp the surgical implant of FIG. 1;

FIG. 9 is a perspective view of the clamping ancillary of FIG. 8 retaining the surgical implant of FIG. 1;

FIG. 10 is a view at a larger scale of the detail X in FIG. 9;

FIGS. 11A and 11B are schematic views at a larger scale of the center of FIG. 4; FIGS. 11A and 11B illustrate two different positions for clamping the surgical implant;

Figure 16:
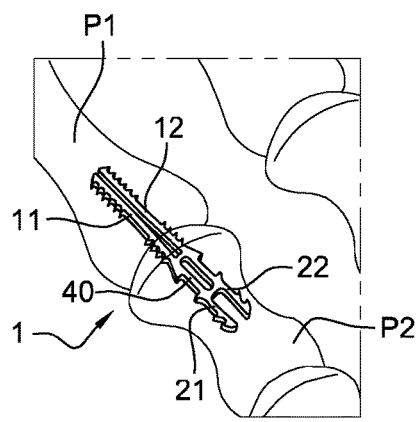
FIG. 16 is a schematic view of the surgical implant of FIG. 1 in the introduction configuration.
Figure 17:
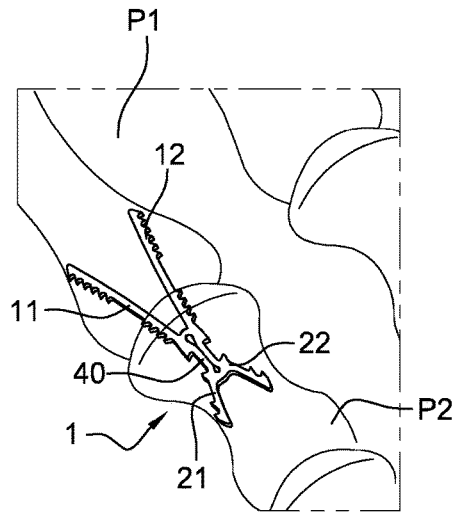
FIG. 17 is a view similar to FIG. 16 illustrating the surgical implant of FIG. 1 in the anchoring configuration.

FIGS. 1, 2, 3, 4, 5 and 6 illustrate a surgical implant 1 intended to enable fusion between a first bone portion and a second bone portion. In the example of FIGS. 16 and 17, the first bone portion and the second bone portion are respectively a proximal phalanx P1 and a middle phalanx P2 of a toe.

The surgical implant 1 comprises a first anchoring portion 10 and a second anchoring portion 20, which are respectively configured to be anchored in the proximal phalanx P1 and in the intermediate phalanx P2.

The first anchoring portion 10 includes two first branches 11 and 12. The first branches 11 and 12 are displaceable between an introduction position (FIGS. 1, 2, 4, 16) and an anchoring position (FIGS. 3, 5, 17).

In the introduction position (FIG. 1, 4, 16), the respective ends 11.1 and 12.1 of the first branches 11 and 12 define a first introduction distance D10.1. The first introduction distance D10.1 is relatively small, so as to enable the introduction of the first branches 11 and 12 inside the proximal phalanx P1, as shown in FIG. 16. In the example of FIGS. 1 to 6, the first introduction distance D10.1 is equal to about 0.4 mm and the first anchoring distance D10.2 is equal to about 6 mm.

In the anchoring position (FIGS. 3, 5, 17), the respective ends 11.1 and 12.1 of the first branches 11 and 12 define a first anchoring distance D10.2 which is larger than the first introduction distance D10.1. Since the first anchoring distance D10.2 is relatively large, the first branches 11 and 12 are adapted to anchor the first anchoring portion 10 inside the proximal phalanx P1.

Figure 4:
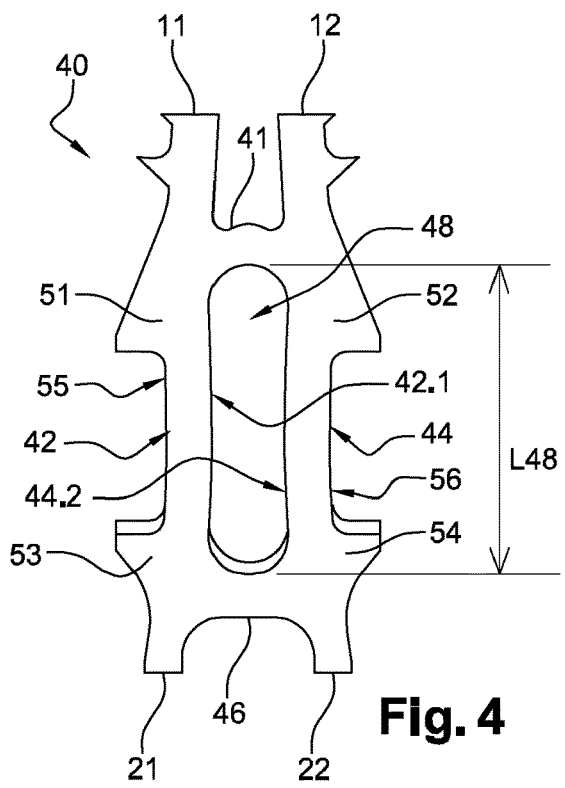
FIG. 4 is a view at a larger scale of the detail IV in FIG. 1.
Figure 5:
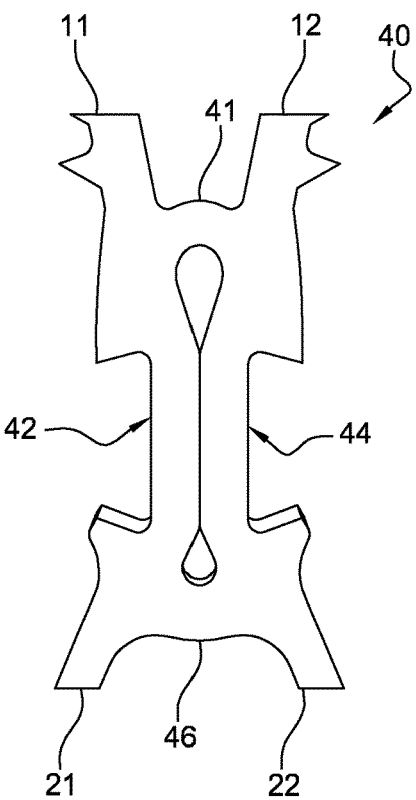
FIG. 5 is a view at a larger scale of the detail V in FIG. 3.
Figure 6:
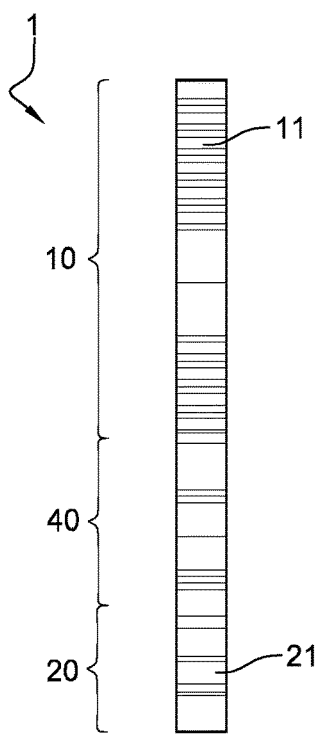
FIG. 6 is a side view of the surgical implant of FIG. 1.

Each of the first branches 11 and 12 have a generally elongated shape and are substantially parallel in their introduction position (FIGS. 1, 4, 16) and substantially form a tightened «U» in their introduction position (FIGS. 1, 4, 16). The first branches 11 and 12 form substantially a «V» in their anchoring position (FIGS. 3, 5, 17), in this instance an angular sector A11.12 of about 30 degrees.

In addition, the surgical implant 1 comprises an intermediate portion 40 which connects the first anchoring portion 10 to the second anchoring portion 20. The intermediate portion 40 extends between the first anchoring portion 10 and the second anchoring portion 20.

The second anchoring portion 20 includes two second branches 21 and 22. Hence, the surgical implant 1 has four branches 11, 12, 21 and 22, namely two on each side of the intermediate portion 40. The second branches 21 and 22 are displaceable between an introduction position (FIGS. 1, 4, 16) and an anchoring position (FIGS. 3, 5, 17).

Each of the second branches 21 and 22 have a generally elongated shape and are substantially parallel in their introduction position (FIGS. 1, 4, 16) and form substantially a tightened «U» in their introduction position (FIGS. 1, 4, 16). The second branches 21 and 22 form substantially a «V» in their anchoring position (FIGS. 3, 5, 17), in this instance an angular sector A21.22 of about 40 degrees.

Hence, the surgical implant 1 has generally a tightened «H» shape when the first branches 11 and 22 and the second branches 21 and 22 are in their introduction positions (FIGS. 1, 4, 16), and an «X» shape when the first branches 11 and 12 and the second branches 21 and 22 are in their anchoring positions (FIGS. 3, 5, 17).

In the introduction position (FIGS. 1, 4, 16), the respective ends 21.1 and 22.1 of the second branches 21 and 22 define a second introduction distance D20.1. The second introduction distance D20.1 is relatively small, so as to enable the introduction of the second branches 21 and 22 inside the intermediate phalanx P2. In the example of FIGS. 1 to 6, the second introduction distance D20.1 is equal to about 1.5 mm and the second anchoring distance D20.2 is equal to about 4.3 mm.

In the anchoring position (FIGS. 3, 5, 17), the respective ends 21.1 and 22.1 of the second branches 21 and 22 define a second anchoring distance D20.2 which is larger than the second introduction distance D20.1. Since the second anchoring distance D20.2 is relatively large, the second branches 21 and 22 are adapted to anchor the second anchoring portion 20 inside the middle phalanx P2.

The intermediate portion 40 includes:
 a first joining portion 41 which joins together the two first branches 11 and 12,
 a first linking portion 42, which is disposed between the first anchoring portion 10 and the second anchoring portion 20, and
 a second linking portion 44, which is disposed between the first anchoring portion 10 and the second anchoring portion 20.

The first linking portion 42 and the second linking portion 44 are arranged on either side of the recess 48 so that the first linking portion 42 is distant from the second linking portion 44. The first linking portion 42 extends substantially between the first branch 11 and the second anchoring portion 20. The second linking portion 44 extends substantially between the second branch 12 and the second anchoring portion 20.

The intermediate portion 40 further includes a recess 48 which herein presents a closed contour. In the example of FIGS. 1 to 6, the recess 48 has an oblong shape, the length L48 of which extends generally between the first anchoring portion 10 and the second anchoring portion 20. The intermediate portion 40 further includes a second joining portion 46 which joins together the second branches 21 and 22. The first linking portion 42 and the second linking portion 44 are arranged on either side of the recess 48. The first linking portion 42 and the second linking portion 44 are arranged respectively on either side of the first joining portion 41 and on either side of the second joining portion 46.

As shown in FIGS. 1 and 4, the closed contour of the recess 48 is defined by the first linking portion 42, by the second linking portion 44, by the first joining portion 41 and by the second joining portion 46.

The intermediate portion 40 is shaped so that an approach between the first linking portion 42 and the second linking portion 44 displaces the first branches 11 and 12 from their introduction position to their anchoring position.

In the example of FIGS. 1 to 6, the intermediate portion 40 is plastically deformable so that a plastic deformation of the intermediate portion 40 bringing the first linking portion 42 closer to the second linking portion 44 displaces the first branches 11 and 12 from their introduction position (FIGS. 1, 4, 16) to their anchoring position (FIGS. 3, 5, 17).

In the example of FIGS. 1 to 5, the plastic deformation of the intermediate portion 40 brings the first linking portion 42 and the second linking portion 44 into contact, thereby displacing the first branches 11 and 12 from the introduction position (FIGS. 1, 4, 16) to the anchoring position (FIGS. 3, 5, 17). As shown in FIGS. 3 and 5, after the plastic deformation, the first linking portion 42 touches the second linking portion 44.

The intermediate portion 40 is composed of a grade 2 titanium allow (titanium T40) according to the standard ISO 5832-2 or ASTM F67. The plastic deformation herein is carried out in the homogeneous plastic deformation domain of the material composing the intermediate portion 40.

The comparison of FIGS. 4 and 5 shows the approximation bringing into contact the first linking portion 42 and the second linking portion 44 resulting from the plastic deformation of the intermediate portion 40.

Similarly to the displacement of the first branches 11 and 12, the intermediate portion 40 is plastically deformable so that a plastic deformation of the intermediate portion 40 bringing the first linking portion 42 closer to the second linking portion 44 displaces the second branches 21 and 22 from their introduction position (FIGS. 1, 4, 16) to their anchoring position (FIGS. 3, 5, 17).

The first branches 11 and 12 are longer than the second branches 21 and 22. The ratio between a length of the first branches 11 and 12 and a length of the second branches 21 and 22 is herein thought to be equal to about 3. The first branches 11 and 12 have the same length. The second branches 21 and 22 have the same length.

The length of each first branch 11 or 12 is herein equal to about 11 mm. The length of each second branch 21 or 22 is herein equal to about 4 mm. The intermediate portion 40 has herein a length, measured along the longitudinal direction of a first branch 11 or 12, equal to about 5 mm. The intermediate portion 40, the first anchoring portion 10 and the second anchoring portion 20 have a thickness E1 equal to about 1.5 mm.

Each first branch 11 or 12 and each second branch 21 and 22 presents, on a respective outer face, notches 11.5, 12.5 and 21.5, 22.5, which are configured to anchor the surgical implant 1 respectively in the proximal phalanx P1 and in the middle phalanx P2. On each end portion of a respective first 11, 12 or second 21, 22 branch, there are notches 11.5, 12.5, 21.5 and 22.5 in the form of harpoons.

In the example of FIGS. 1 to 6, the surgical implant 1 is monolithic. Hence, like the intermediate portion 40, the first branches 11 and 12 and the second branches 21 and 22 are composed of a grade 2 titanium alloy according to the standard ISO 5832-2 or ASTM F67.

As shown in FIGS. 3 and 5, after the plastic deformation, the first linking portion 42 touches the second linking portion 44, in such a manner that the recess 48 is reduced or even non-existent.

The first linking portion 42 presents a first face 42.1 which is convex and which is oriented toward the second linking portion 44. The first face 42.1 has a profile formed by an arc of circle the radius of which is herein equal to about 35 mm.

Similarly, the second linking portion 44 presents a second face 44.2 which is convex and which is oriented toward the first linking portion 42. The second face 44.2 has a profile formed by an arc of circle the radius of which is herein equal to about 35 mm.

In addition, the intermediate portion 40 further includes four abutments 51, 52, 53 and 54 which extend in protrusion on two respective outer faces 55, 56 of the intermediate portion 40 which are opposite to each other. The abutments 51 and 52 extend in protrusion on the outer face 55, and the abutments 53 and 54 extend in protrusion on the outer face 56. The two abutments 51 and 52 are located on the side of the first branches 11 and 12, whereas the abutments 53 and 54 are located on the side of the second branches 21 and 22.

Each outer face 55 or 56 of the intermediate portion 40 presents, next to the abutments 51, 52, 53, 54, non-represented friction means, notches or roughnesses, which are configured to grip, by friction, the jaws of a clamping ancillary.

Figure 7:
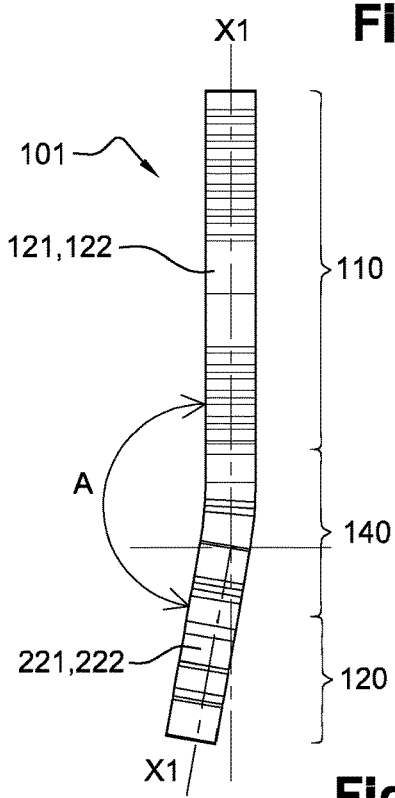
FIG. 7 is a view similar to FIG. 6 of a surgical implant in accordance with a variant of the invention.
Figure 12:
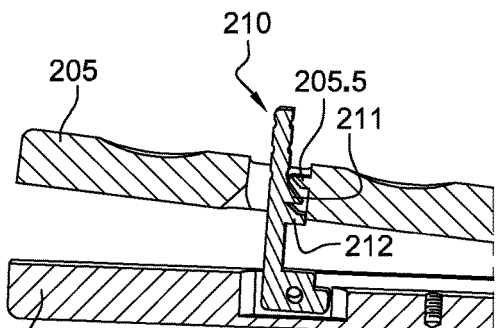
FIG. 12 is a side view of a portion of the clamping ancillary of FIG. 8 in an open position.

FIG. 7 illustrates a surgical implant 101 in accordance with a variant of the invention. The surgical implant 101 is similar to the surgical implant 1, with the exception of the notable differences mentioned hereinafter. The surgical implant 101 comprises a first anchoring portion 110, a second anchoring portion 120 and an intermediate portion 140. The first anchoring portion 110 includes two first branches 111 and 112 similar to the first branches 11 and 12 of the surgical implant 1. The second anchoring portion 120 includes two second branches 121 and 122 similar to the second branches 21 and 22 of the surgical implant 1.

The surgical implant 101 differs from the surgical implant 1, because the first branches 111 and 112 extend along a first longitudinal direction X1, whereas the second branches 121 and 122 extend along a second longitudinal direction X2. Thus, the first branches 111 and 112 and the second branches 121 and 122 form together an angle A.

The angle A is herein equal to about 170 degrees in a plane containing the first longitudinal direction X1 and the second longitudinal direction X2. The angle A is herein represented in the plane of FIG. 7, which is parallel to the plane containing the first longitudinal direction X1 and the second longitudinal direction X2.

FIGS. 8, 9, 10, 12, 13, 14 and 15 illustrate a clamping ancillary 200 in accordance with the invention, which is configured to clamp the surgical implant 1 or 101. The clamping ancillary 200 comprises two jaws 201 and 202 and a joint 204. The joint 204 connects the jaws 201 and 202. The clamping ancillary 200 further comprises two gripping bars 205 and 206. Each gripping bar 205 or 206 is secured to a respective jaw 201 or 202.

Each jaw 201 or 202 defines a respective housing 201.1 or 202.1 having a shape complementary to a respective linking portion 42 or 44, so that each jaw 201 or 202 can grip a respective outer face 55 or 56 of the intermediate portion 40. In the example of FIGS. 1 to 6, each of the first linking portion 42 and of the second linking portion 44 have a section with a rectangular profile. Hence, in the example of FIGS. 8 to 15, each respective housing 201.1 or 202.1 defined by the jaws 201 and 202 is generally parallelepipedic with a rectangular profile open on one side, as shown in FIG. 8.

The joint 204 is configured so that a displacement of the jaws 202 and 204 results in a plastic deformation of the intermediate portion 40 bringing the first linking portion 42 closer to the second linking portion 44.

The joint 204 includes a latch 210 which presents two locking notches 211 and 212. The jaw 205 presents a lug 205.5 configured to cooperate with the locking notches 211 and 212 by form-fitting. The latch 210 is linked to the jaw 206 by a pivot link 214. The latch 210 presents a handling portion 210.1, which is configured to allow a surgeon to handle the latch 210 so as to move the joint 204.

The joint 204 is movable between:
- an open position (FIGS. 8 and 12), in which the jaws 201 and 202 define a space 215 enabling the installation of the surgical implant 1; in the open position, the lug 205.5 does not cooperate yet with the locking notches 211 and 212;
- a retaining position (FIGS. 9, 10 and 13), in which the jaws 201 and 202 grip the respective outer faces 55 and 56 of the intermediate portion 40 so that the clamping ancillary 200 retains the surgical implant 1; in the retaining position, the lug 205.5 is engaged between the locking notches 211 and 212;
- a clamping position (FIG. 15), in which the jaws 201 and 202 clamp the intermediate portion 40 so as to achieve the intended plastic deformation; in the clamping position, the lug 205.5 is cleared from the locking notches 211 and 212, so that the lug 205.5 is located below the locking notches 211 and 212.

Figure 13:
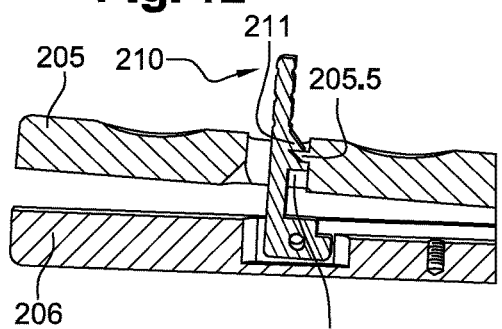
FIG. 13 is a view similar to FIG. 12 illustrating the clamping ancillary of FIG. 12 in a retaining position.
Figure 14:
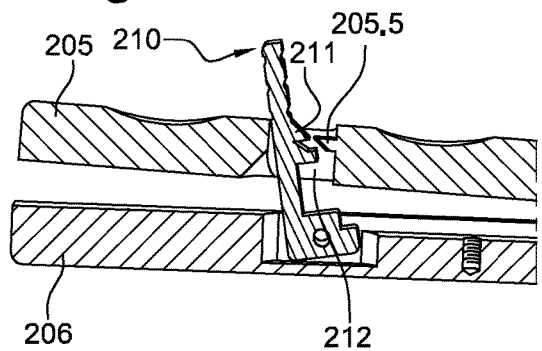
FIG. 14 is a view similar to FIG. 12 illustrating the clamping ancillary of FIG. 12 in a position following the clamping position of FIG. 13.
Figure 15:
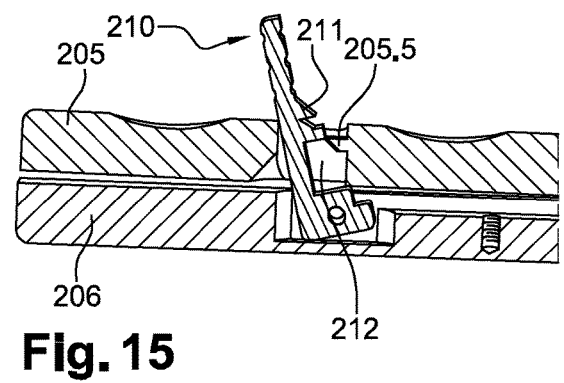
FIG. 15 is a view similar to FIG. 12 illustrating the clamping ancillary of FIG. 12 in a clamping position.

Thanks to the handling portion 210.1, the surgeon can handle the latch 210 so as to move the joint 204 between the open position (FIGS. 8 and 12), the retaining position (FIGS. 9, 10 and 13) and the clamping position (FIG. 15). The figure illustrates the clamping ancillary 200 in a position following the clamping position (FIG. 13).

FIG. 11A illustrates a first clamping position of the surgical implant 1 with respect to the ancillary one 200. The resultant of the clamping forces exerted by the jaws 201 and 202 on the surgical implant 1 is generally carried by a resultant axis A.

In this first clamping position, the resultant axis A passes substantially through the middle of the recess 48, along a longitudinal direction generally defined by the first branches 11 and 12 in the introduction positions (FIGS. 1, 2 and 4).

In this first clamping position, the clamping forces exerted by the jaws 201 and 202 on the surgical implant 1 are uniformly distributed on the intermediate portion 40. Thus, the plastic deformation of the first branches and of the second branches could be symmetrical in the case where the first branches and the second branches are symmetrical.

FIG. 11B illustrates a second clamping position of the surgical implant 1 with respect to the ancillary one 200. The resultant of the clamping forces exerted by the jaws 201 and 202 on the surgical implant 1 is generally carried by the resultant axis A.

In this second clamping position, unlike the first clamping position illustrated in FIG. 11A, the resultant axis A does not pass through the middle of the recess 48, but closer to the second anchoring portion 20.

In this second clamping position, the clamping forces exerted by the jaws 201 and 202 on the surgical implant 1 are not uniformly distributed on the intermediate portion 40. Thus, the plastic deformation of the first branches and of the second branches is not symmetrical. The second branches would be spaced apart further than the first branches.

FIGS. 16 and 17 illustrate the surgical implant 1 respectively before and after the plastic deformation of the intermediate portion 40, therefore respectively before and after spacing apart the first branches 11 and 12 and of the second branches 21 and 22. Hence, FIG. 16 illustrates the first branches 11 and 12 and the second branches 21 and 22 in their introduction positions, whereas FIG. 17 illustrates the first branches 11 and 12 and the second branches 21 and 22 in their anchoring positions.

Of course, the present invention is not limited to the particular examples described in the present application. Other embodiments within the reach of those skilled in the art may also be considered without departing from the scope of the present invention.

The invention claimed is:

1. A surgical implant, intended to enable fusion between a first bone portion and a second bone portion, the surgical implant comprising at least:
    a first anchoring portion configured to be anchored in the first bone portion, the first anchoring portion including at least two first branches the first branches being displaceable between:
    an introduction position, in which the respective ends of the first branches define a first introduction distance, so as to enable the introduction of the first branches inside the first bone portion, and
    an anchoring position, in which the respective ends of the first branches define a first anchoring distance larger than the first introduction distance, so that the first branches are adapted to anchor the first anchoring portion inside the first bone portion,
    a second anchoring portion configured to be anchored in the second bone portion,
    an intermediate portion connecting the first anchoring portion to the second anchoring portion;
    the surgical implant wherein:
    the intermediate portion includes at least:
    a recess,
    a first linking portion disposed between the first anchoring portion and the second anchoring portion, and
    a second linking portion disposed between the first anchoring portion and the second anchoring portion the first linking portion and the second linking portion being arranged on either side of said at least one recess so that the first linking portion is distant from the second linking portion and
    the intermediate portion is shaped so that bringing together the first linking portion and the second linking portion displaces the first branches from their introduction position to their anchoring position.

2. The surgical implant according to claim 1, wherein the second anchoring portion includes at least two second branches, the second branches being displaceable between:
    an introduction position, in which the respective ends of the second branches define a second introduction distance, so as to enable the introduction of the second branches inside the second bone portion, and an anchoring position, in which the respective ends of the second branches define a second anchoring distance larger than the second introduction distance so that the second branches are adapted to anchor the second anchoring portion inside the second bone portion, wherein the intermediate portion is shaped so that bringing together the first linking portion and the second linking portion displaces the second branches from their introduction position to their anchoring position.

3. The surgical implant according to claim 1, wherein the intermediate portion is plastically deformable so that a plastic deformation of the intermediate portion bringing together the first linking portion and the second linking portion displaces the first branches and/or the second branches from their introduction position(s) to their anchoring position(s).

4. The surgical implant according to claim 1, wherein the intermediate portion is elastically deformable so that an elastic expansion of the intermediate portion bringing together the first linking portion and the second linking displaces the first branches and/or the second branches from their introduction position(s) to their anchoring position(s).

5. The surgical implant according to claim 1, wherein each of the first branches has a generally elongated shape, and wherein the first branches are substantially parallel in their introduction position and form substantially a «V» in their anchoring position.

6. The surgical implant according to claim 2, wherein the intermediate portion further includes a first joining portion joining at least two first branches a second joining portion joining at least two second branches the first linking portion and the second linking portion being arranged respectively on either side of the first joining portion and on either side of the second joining portion.

7. The surgical implant according to claim 1, wherein at least one recess has an oblong shape, the length of which extends generally between the first anchoring portion and the second anchoring portion.

8. The surgical implant according to claim 1, wherein at least one recess presents a narrow area and a large area which is larger than the narrow area, the widths being measured between the first linking portion and the second linking portion.

9. The surgical implant according to claim 1, wherein the first linking portion presents a first face which is convex and which is oriented toward the second linking portion, the first face having a profile formed by an arc of circle the radius of which is larger than 20 mm, and wherein the second linking portion presents a second face which is convex and which is oriented toward the first linking portion, the second face having a profile formed by an arc of circle the radius of which is larger than 20 mm.

10. The surgical implant according to claim 1, wherein at least the intermediate portion is composed of a material selected in the group constituted by:

a titanium alloy, according to the standard ISO 5832-2 or ASTM F67, and a stainless steel according to the standard ISO 58321.

11. The surgical implant according to claim 1, wherein the intermediate portion further includes at least two abutments extending in protrusion on two opposite outer faces of the intermediate portion.

12. A clamping ancillary configured to clamp at least one surgical implant according to claim 1, the clamping ancillary comprising at least two jaws and at least one joint connecting said at least two jaws the clamping ancillary wherein each jaw presents a respective housing having a shape complementary to a respective linking portion so as to grip a respective outer face of the intermediate portion, and in that said at least one joint is configured so that a displacement of the jaws results in bringing together the first linking portion and the second linking portion.

13. The clamping ancillary according to claim 12, wherein said at least one joint includes a latch presenting at least one locking notch, the joint being movable between:

an open position, in which the jaws define a space allowing the installation of the surgical implant, a retaining position, in which the jaws grip the respective outer faces of the intermediate portion so that the clamping ancillary retains the surgical implant, a clamping position, in which the jaws clamp the intermediate portion so as to obtain said approach.

14. The clamping ancillary according to claim 13, wherein the latch is linked to one of the jaws by a pivot link, and wherein the latch presents a handling portion, configured to allow a surgeon to handle the latch so as to move the joint between the open position, the retaining position and the clamping position.

* * * * *